United States Patent [19]
Thierman et al.

[11] Patent Number: 5,967,990
[45] Date of Patent: Oct. 19, 1999

[54] SURGICAL PROBE COMPRISING VISIBLE MARKINGS ON AN ELASTIC MEMBRANE

[75] Inventors: Jonathan Thierman, Cambridge; Roger W. Brockett, Lexington, both of Mass.; Nicola J. Ferrier, Madison, Wis.

[73] Assignee: President and Fellows of Harvard College, Cambridge, Mass.

[21] Appl. No.: 09/133,242

[22] Filed: Aug. 13, 1998

[51] Int. Cl.⁶ ..................................................... A61B 8/14
[52] U.S. Cl. ............................ 600/459; 600/466; 604/96
[58] Field of Search .................................. 600/463, 443, 600/444, 445, 450, 459, 461–462, 426, 476, 117, 175; 606/194, 1; 604/96, 103

[56] References Cited

U.S. PATENT DOCUMENTS

| | | |
|---|---|---|
| 4,834,070 | 5/1989 | Saitou . |
| 4,980,646 | 12/1990 | Zemel . |
| 5,054,492 | 10/1991 | Scribner et al. ........................ 600/463 |
| 5,099,850 | 3/1992 | Matsui et al. ............................ 600/463 |
| 5,259,837 | 11/1993 | Van Wormer ............................. 604/96 |
| 5,459,329 | 10/1995 | Sinclair . |
| 5,860,923 | 1/1999 | Lenker et al. ........................... 600/433 |

OTHER PUBLICATIONS

R.W. Brockett, "Robotic Hands With Rheological Surfaces" 5 pages.

Nicola J. Ferrier, Kristi A. Morgansen, Dimitris Hristu, "Implementation of Membrane Shape Reconstruction" Harvard University, 64 pages (1997).

R. Andrew Russell, "A Nephelometric Tactile Sensor" 9 pages.

Jonathan Thierman "Surgical Probe for the Detection of Pulsing Blood Vessels and Embedded Lesions" 33 Pages, Engineering Senior Design Thesis, Harvard University (1998).

*Primary Examiner*—Scott M. Getzow
*Assistant Examiner*—Ali M. Imam
*Attorney, Agent, or Firm*—Choate, Hall & Stewart

[57] ABSTRACT

Surgical probe for use in minimally invasive surgery. The probe includes an elastic membrane tip portion which deforms upon contact with an object. The elastic membrane forms an enclosure containing fluid and an inside surface of the membrane includes a plurality of visible markings such as dots. A CCD camera forms an image of the dots and the image of the dots or a representation of the image of the dots is displayed on a video monitor. The probe also includes an ultrasound transducer which responds to frequency shifts to indicate motion of an object reflecting ultrasound energy. A speaker generates sounds related to the frequency shift as an indication of motion. The probe thus provides information about the surface of an object encountered during a minimally invasive procedure and also about motion of structures within the body.

12 Claims, 3 Drawing Sheets

SURGICAL PROBE COMPRISING VISIBLE MARKINGS ON AN ELASTIC MEMBRANE

The Government has rights in this invention pursuant to O.N.R. Grant No. N00014-90-J-1887.

BACKGROUND OF THE INVENTION

This invention relates to a surgical probe and more particularly to a surgical probe for the detection of embedded anatomical structures and pulsing blood vessels.

Historically, surgery has been a physically traumatic experience. Surgical techniques often involved large incisions in the body to allow the surgeon both to see and feel organs and tissues that were being removed or repaired. While medicine in general has flourished in the 20th Century with innovations such as penicillin and x-ray machines, surgery has not progressed technologically nearly so quickly as other fields of medicine. Until the early 1980's the most significant surgical advance had been the invention of general anesthesia in 1846.

The early 1980's began what has become a revolution in surgery called minimally invasive surgery (MIS). This revolution in surgery in turn resulted in large measure from the development of imaging techniques employing cameras with charge coupled devices (CCD) as the image capturing element. CCD elements are very small (3.4 mm by 6 mm is standard) and can be used to make tiny cameras because they allow the image to be digitized at the camera lens but processed by electronics which may be separated from the camera itself.

In minimally invasive surgery, the surgeon makes several small (1–2 cm) incisions in the body and uses long, slender tools such as endoscopic forceps and scalpels, inserted through small incisions, to manipulate tissue inside the body. The surgeon watches what he or she is doing on a video monitor. The image on the monitor is generated by an endoscope, a long slender camera/lens system typically 10 mm in diameter, which is inserted through one of the incisions.

Minimally invasive surgery reduces trauma to the patient, greatly reduces patient recovery time and leaves very little scarring. The first procedure routinely performed by minimally invasive surgery was removal of the gall bladder. This procedure is known as cholecystectomy.

Despite the great medical promise of minimally invasive surgery, the technique is still in its infancy due in large measure to the fact that the surgeon has virtually no sense of touch during such procedures. Instead, the surgeon must rely purely on visual feedback from the endoscope to ensure that he or she is performing the tasks properly. For most procedures, tactile feedback is crucial in order to manipulate properly delicate body tissues and to diagnose correctly the state of disease. Further, surgeons must take great care during minimally invasive procedures not to puncture accidentally an embedded blood vessel that is not visible in the endoscope image. Tumors are also difficult to locate visually during minimally invasive surgery.

The lack of tactile feedback is a great disadvantage in the case of cholecystectomy. The gall bladder is removed usually because the bile ducts have been blocked by stones that often develop in elderly patients at the junction between the gall bladder and the cystic duct. Because the cystic duct and cystic artery are often directly next to each other, they may be indistinguishable by visual observation provided by an endoscope. Surgical complications often result and a significant number of laproscopic cholecystectomies are converted to open cholecystectomy in order to give the surgeon a better visual field.

Modem surgical instruments for minimally invasive surgery include high resolution endoscopic camera systems and high quality endoscopes for imaging during the procedure. The tools most frequently used by surgeons are the endoscopic scalpel, forceps, and grasps. Although some tactile array sensors have been adapted to surgical probes, they are not routinely used in surgery. This lack of routine use may be due to their rigid structure that does not lend itself well to tactile sensing of curved geometries such as human organs.

Surgeons have also used invasive Doppler probes in heart studies and in invasive imaging techniques. Such pulsed Doppler systems are electronically complex because they rely on precisely timed circuitry to parse the incoming and outgoing signals. Simpler ultrasonic devices are known for detecting flow. Such devices use the Doppler effect with a continuous wave ultrasonic signal. Such devices have been used to determine information on blood flow in surface arteries.

Currently, there are no devices known to the inventors that can detect motion or flow so as to localize pulsing blood vessels and also provide a representation of the shape of an object within the body.

SUMMARY OF THE INVENTION

The surgical probe according to the invention includes an elongate tube having a tip portion. The tip portion includes an elastic membrane forming an enclosure that contains a fluid therein such as water or gel or air. Thus the fluid may be either incompressible or compressible. The inside surface of the membrane has a plurality of visible markings arranged in a desired pattern. The tube interior includes apparatus for illuminating the markings on the inside surface of the membrane and also includes apparatus for forming a two-dimensional image of the markings. The image forming apparatus may be a camera within the tube or fiber optics for delivering an image to a camera outside the tube or a combination of fiber optics and a camera. Disposed within the tube is a first ultrasound transducer for propagating ultrasound energy through the fluid-filled membrane for interaction with and reflection from an object outside of the enclosure. A second ultrasound transducer is included within the tube for receiving the ultrasound energy reflected from the object. The system further includes a visual monitor for displaying the markings themselves or a representation derived from the markings to indicate surface topography of a structure in contact with, and deforming, the outside surface of the membrane. Also included is a speaker for generating sound related to a frequency shift of the ultrasound energy reflected from the object to indicate motion of the object with respect to the probe. The object receiving ultrasound energy and the structure deforming the membrane may be the same or different entities within the body.

A preferred embodiment of the invention also includes a computer for receiving the image from the camera and programmed to generate a wire-frame representation of the surface topography. It is preferred that the visible markings be dots arranged in a regular array. A suitable camera is a charge coupled device (CCD). It is also preferred that the ultrasound energy be continuous wave ultrasound centered at a frequency of approximately 5 MHz. Another embodiment simply presents an image of the markings on the membrane to the surgeon via a video screen allowing the surgeon to infer the shape from movement of the markings.

The surgical probe of the invention provides a surgeon with tactile feedback by providing a representation of the surface topography of a structure within the body which comes into contact with the probe. Further, the surgeon is provided audible information indicating the state of motion of objects encountered within the body. Thus, the probe of the invention enhances a surgeon's ability to distinguish structures within the body such as the ability to discriminate between the cystic duct of the gall bladder and pulsing flow in the cystic artery during a cholecystectomy procedure.

Yet another aspect of the invention is shape reconstruction apparatus including an elastic membrane forming an enclosure and containing a compressible or incompressible fluid therein, an inside surface of the membrane including a plurality of visible markings. Imaging apparatus forms a two-dimensional image of the markings and a visual display displays the markings or a representation derived from the markings to indicate surface topography of a structure in contact with, and deforming, the elastic membrane. This aspect of the invention can be used in applications other than in a surgical context such as, for example, determining shape for use in remote manipulation.

DESCRIPTION OF THE PREFERRED EMBODIMENT

Figure 1:
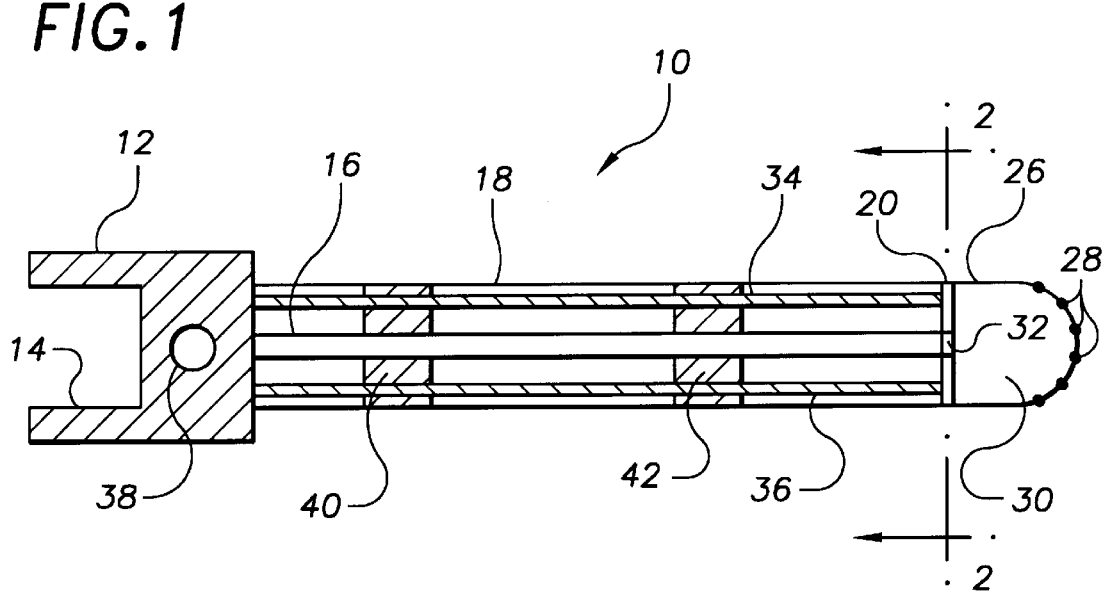
FIG. 1 is a cross-sectional view of the surgical probe of the invention.

First of all, the theory on which the surgical probe of the invention is based will be discussed. Endoscopes used in modem minimally invasive surgery typically utilize CCD cameras which record a two-dimensional projection of objects within the camera's field of view. Information about the third dimension is lost in such a projection. A methodology for reconstructing shape from a single two-dimensional image has been developed at the Harvard Robotics Laboratory in Cambridge, Mass. This method uses a fluid-filled elastic membrane as a sensor for shape reconstruction. The fluid may be compressible or incompressible. Black dots drawn in a matrix pattern on the inside surface of the fluid-filled membrane move as the membrane deforms upon encountering objects on its outer surface. The method is an example of biomimetics in that the shape reconstruction sensor is designed to mimic an actual fluid filled human finger tip.

The algorithm for reconstructing shape relies on methods of projective geometry, differential equations and matrix algebra. See, N. J. Ferrier, K. A. Morgansen, D. Hristu, "Implementation of Membrane Shape Reconstruction," Technical Report 97-1, Harvard Robotics Lab, Harvard University (1997), the contents of which are incorporated by reference herein. As disclosed in this Technical Report, information about two dimensions x and y is recorded directly onto the CCD element of the camera. In order to determine the z component of each dot's position, a constant volume constraint coupled with a minimum energy constraint and a fixed boundary condition are sufficient to limit the infinite number of solutions to one unique solution. The method depends on a fluid-filled, elastic membrane in which a fluid establishes a constant volume and the elasticity of the membrane allows for the application of an energy minimizing constraint. The algorithm is processed in a computer which generates an animated wire-frame model of the shape of the deformed membrane which thus provides information about the object deforming the membrane.

The other major aspect of the probe relates to Doppler velocimetry. Doppler velocimetry is commonly used in medical applications to detect and diagnose blood flow in fetal monitoring and in arterial disease. Doppler velocimetry is based on the well known Doppler effect in which waves reflected from a moving object undergo a frequency shift. The shift is proportional to the speed of the moving object and is a result of the fact that the moving object reflects the waves that it encounters at the frequency at which it encounters them, not at the original frequency at which they were sent. Thus, if an object is moving toward the wave source with a given velocity, it will encounter more waves per second then if it were standing still. The object will reflect this increased frequency to the source. The frequency shift can be measured between the reference wave which is propagated toward the object, and the frequency shifted wave that is reflected.

Doppler probes have been used for many years for fetal heart rate monitoring as well as non-invasive blood flow diagnosis on patients with heart disease. Although the interpretation of the output of Doppler probes is subjective, an experienced vascular specialist can accurately diagnose blood vessel characteristics from the sound of a Doppler signal. For example, phasicity, which refers to the direction of blood flow, can be determined from a Doppler signal. In addition, a vascular expert is able to detect an arterial obstruction by listening to the Doppler signal and hearing the healthy "one-two-three" swishing sound deteriorate into a "one-two" swishing sound. These two sounds are referred to as a triphasic waveform and a biphasic waveform because they have either three or two distinct phases for each pulse of blood. Similarly, a monophasic waveform in which only one swishing sound is heard per beat indicates more advanced arterial disease. As will be seen below, the output of the surgical probe of the invention is an audible signal from which motion can be inferred coupled with a visual display which provides shape reconstruction information.

With reference now to FIG. 1, a surgical probe 10 includes a casing 12 including a recessed portion 14. The casing 12 is designed to the exact shape of an eyepiece of a two millimeter standard endoscope (not shown). An inner steel channel 16 is attached to the casing 12 and serves as a channel to guide an endoscope through the probe 10. The inner channel 16 is approximately 255 mm long, 3 mm OD and 2.2 mm ID. It is preferred that this channel be made of 316 steel tube which is FDA approved as body implantable. The inner steel channel 16 is disposed within an outer probe tubing 18 which is also preferably made of 316 stainless steel. It is preferred that the outside diameter of the outer probe tubing 18 be 10 mm with an inside diameter of 7 mm. A 10 mm outside diameter is preferred because trocars, which are tunnels through which minimally invasive tools enter the body, are made in sizes only up to 10 mm in diameter. The 7 mm inside diameter provides a suitable wall thickness for a rigid probe. A polystyrene window 20 resides in a shelf in the end of the outer probe tubing 18. The polystyrene window 20 is approximately 0.259 inches in diameter and was machined from 0.05 inches thick clear polystyrene.

Figure 2:
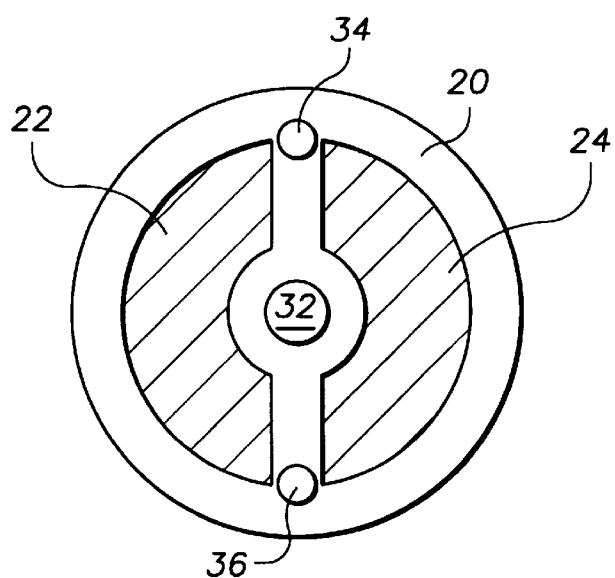
FIG. 2 is a cross-sectional view of the probe of FIG. 1 taken along lines 2—2.

As shown in FIG. 2, ultrasound transducers 22 and 24 are disposed on the polystyrene window 20. Polystyrene is used for the window 20 because polystyrene has good acoustical coupling with 5 MHz ultrasound crystals such as the ultrasound transducers 22 and 24.

Attached to the end of the outer probe tubing 18 is an elastic membrane 26. A suitable elastic membrane 26 is a ⅜ inch diameter by 2 inches long pipe seal available from North American Latex Company of Sullivan, Ind. The preferred pipe seal was created in a special run with two dips in white and then two dips in black latex so that it is both opaque and yet provides good contrast for black dots 28 on a white inside surface. It is preferred that the elastic membrane 26 be part of a replaceable tip structure for replacement as needed. The black dots 28 were placed on the membrane 26 by mounting the latex membrane in the vice of a numerically controlled milling machine. A waterproof ink pen was placed in the collet of the milling machine instead of a normal milling bit. The pen applied dots to the membrane in a 3×3 grid according to commands given to the computer connected to the milling machine. The position of the dots 28 was recorded from the computer controlling the machine. It is preferred that the elastic membrane 26 be filled with an incompressible fluid such as an RTV gel 30.

With reference now to FIGS. 1 and 2, a charge coupled device camera 32 is positioned within an opening in the polystyrene window 20. Alternatively, the camera 32 may be remotely located and light delivered to the camera 32 by, for example, a fiber optic bundle (not shown). The camera 32 forms a part of an endoscope (not shown) which slides through the inner steel channel 16. The camera 32 is adapted to create an image of the dots 28 on the inner surface of the elastic membrane 26. Optical fibers 34 and 36 illuminate the inside surface of the membrane 26 allowing the camera 32 to form an image of the black dots 28. More than two optical fibers may be provided if desired.

The response of the ultrasound transducer crystals 22 and 24 were selected to be centered in the 5 MHz frequency range in order to penetrate tissue to a depth of 1–3 cm. Lower frequencies do not penetrate as deeply and higher frequency result in greater signal attenuation. This frequency range also works well with electronics that drive them. Those skilled in the art will appreciate that it is important to maximize the area of the crystals 22 and 24 since the depth of penetration is directly proportional to crystal area. Suitable crystals 22 and 24 are PZt transducer material available from Nicolet Vascular Inc. of Golden, Colo. The crystals normally come in half disk shapes and so a special design was ordered to provide the opening for the camera 32. In this way, surface area was maximized while providing a line of sight through the center of the crystals 22 and 24 for the endoscope camera 32. Prism 401 glue available from the Locktight Corporation was used to adhere the crystals 22 and 24 to the polystyrene window 20. This glue has good acoustical coupling properties. As will be appreciated by those skilled in the art, electrical leads for energizing the transducer crystals 22 and 24 are provided and access is obtained through an opening 38 in the casing 12. The optical fibers 34 and 36 may also pass through the opening 38. Acrylic spacers 40 and 42 are provided for centering the inner steel channel 16 and to guide the optical fibers 34 and 36 and leads (not shown) from the transducer crystals 22 and 24. Care must be taken to minimize tensile stresses in the thin transducer leads.

The electronics (not shown) for the Doppler transducers were generated and processed by integrated circuits designed by Nicolet Vascular, Inc. and used in the Pocket-Dop II handheld Doppler device. It is also preferred that the electronics be battery powered in order to eliminate the risk of accidental electrical shock during a surgical procedure. It is also preferred that the camera 32 protrude slightly through the opening in the window 20 to minimize glare. It is also preferred that a multistrand fiber optic bundle be used for illuminating the inside surface of the membrane 26. Further details of a design prototype of the probe 10 are provided in Thierman, Jonathan, "Surgical Probe for the Detection of Pulsing Blood Vessels and Embedded Lesions," Harvard University Engineering Senior Design Thesis (1998), the contents of which are incorporated herein by reference.

Figure 3:
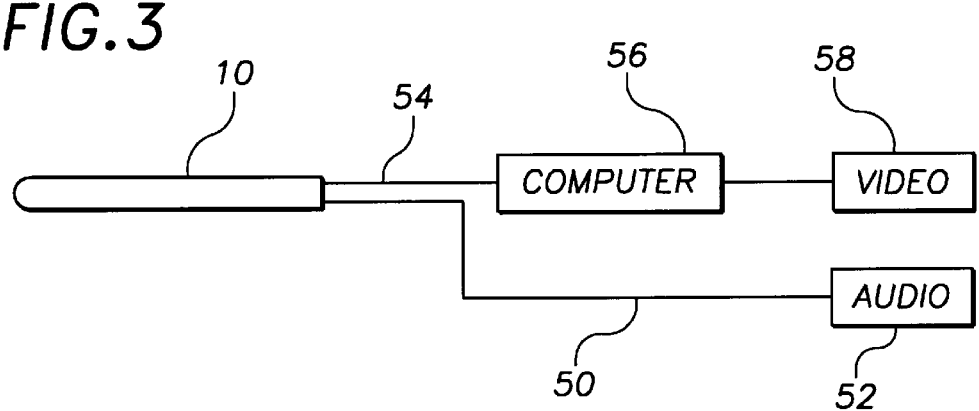
FIG. 3 is a block diagram of the surgical probe system of the invention.
Figure 4A:
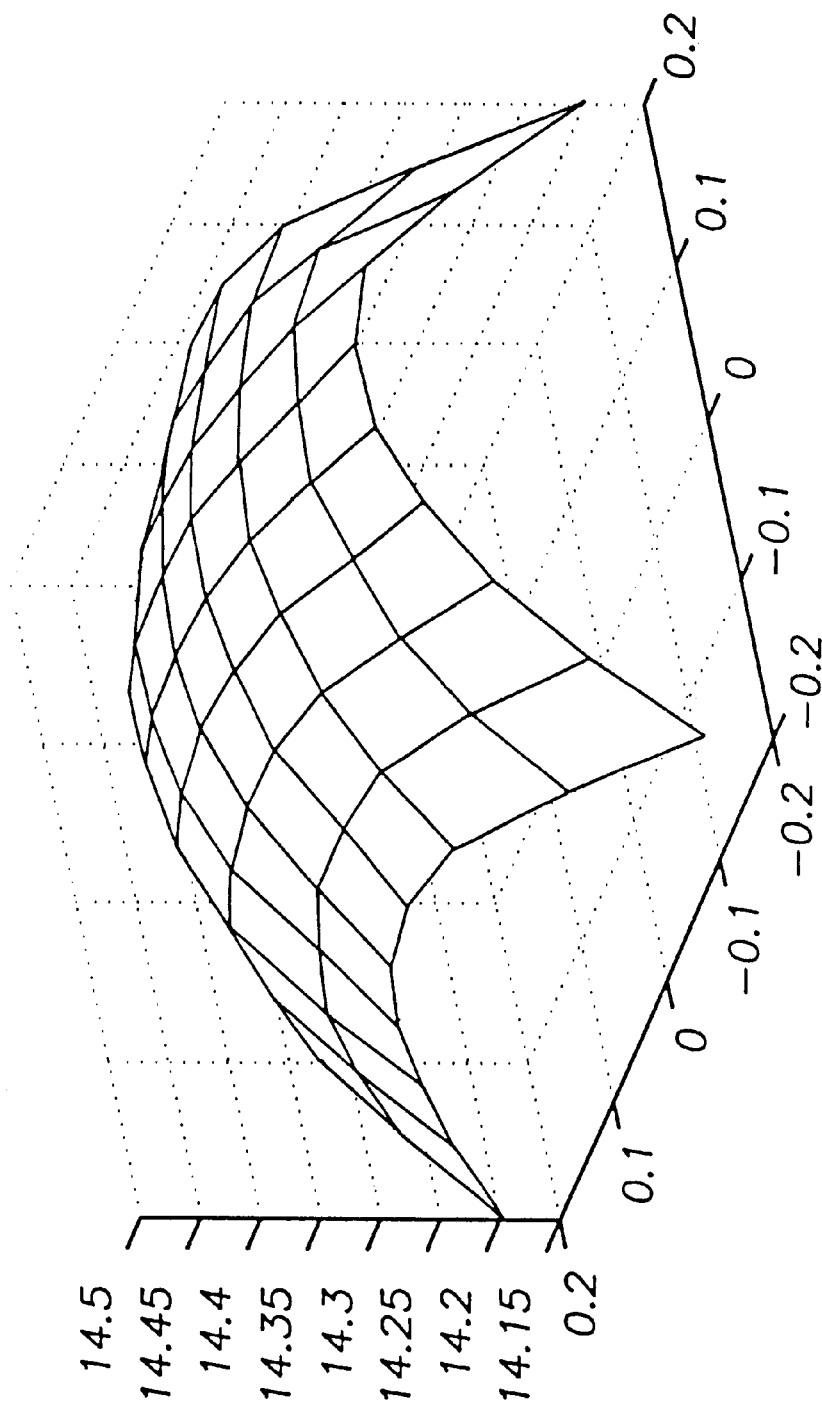
FIGS. 4a and 4b are graphs showing reconstructed surfaces of the probe tip.
Figure 4B:
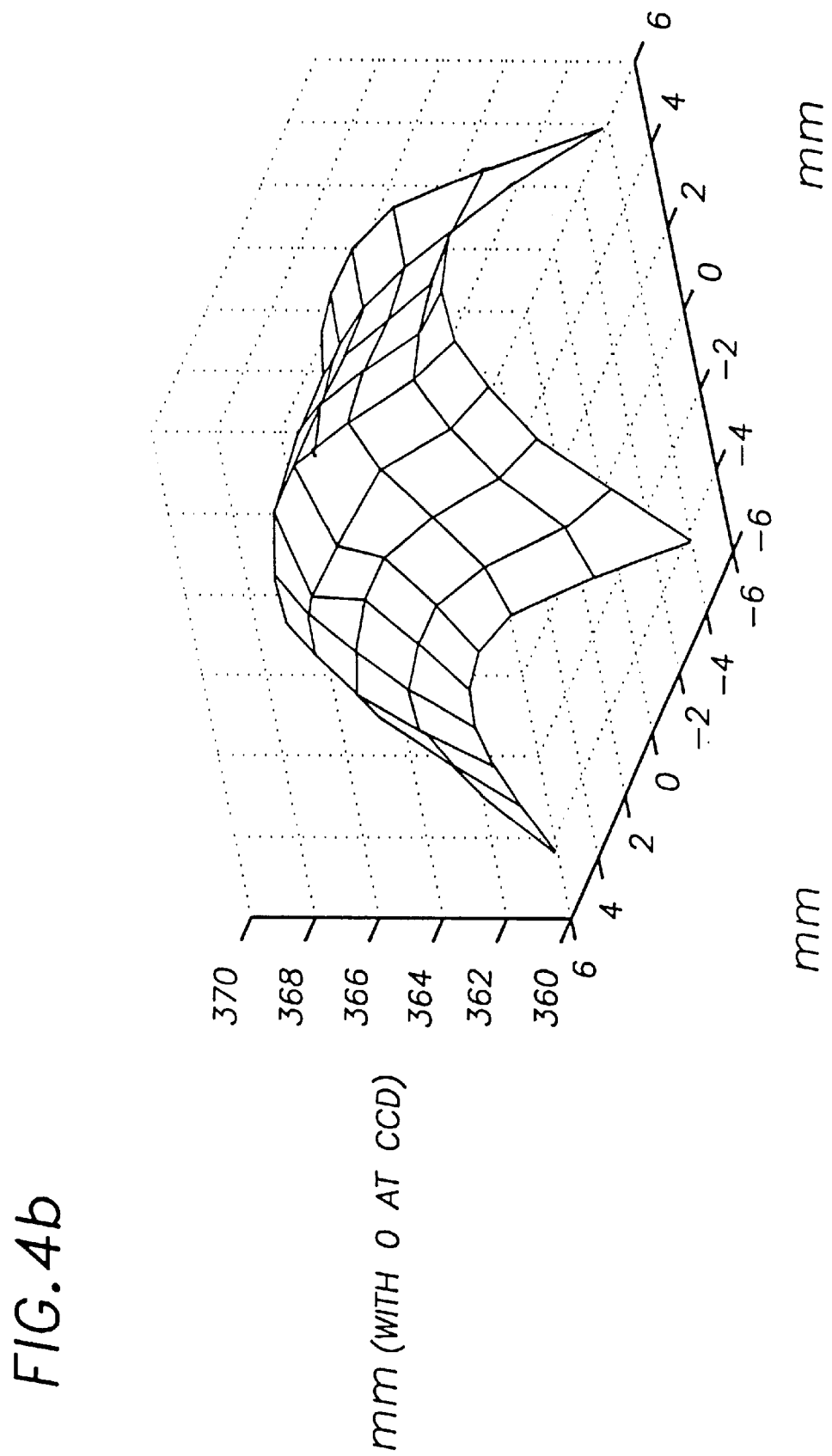

With reference now to FIG. 3, an output 50 from the Doppler portion of the probe 10 is applied to an amplified speaker 52 which produces sounds characteristic of velocity of an object being interrogated. An output 54 from the shape reconstruction portion of the probe 10 is processed by a computer 56 and displayed on a video monitor 58. The monitor 58 may display the raw image of the dots 28 in which case the surgeon infers shape directly from motion of the dots. Alternatively, the computer 56 may process the signal 54 using the reconstruction algorithm discussed above to generate animated wire frame representations. FIGS. 4a and 4b show shape reconstruction for an undeformed membrane (FIG. 4a) and for a deformed membrane (FIG. 4b).

In use, the probe 10 is inserted into a surgical field through a trocar. The inner steel channel 16, attached to the casing 12, serves as a channel to guide the endoscope through the probe 10. The surgeon watches the video display 58 which provides tactile feedback by showing the surface topography of an object encountered by the deformable tip of the probe. The surgeon also listens to the audio presented by the speaker 52 to ascertain the sounds consistent with the motion of, for example, flowing blood or a pulsing blood vessel. The combination of the video and audio information enables the surgeon to distinguish between the cystic duct and the cystic artery during the cholecystectomy procedure as one prime example of the use of the probe of the invention.

The shape reconstruction and Doppler velocimetry aspects of the invention work together exceptionally well in the surgical probe. The shape reconstruction portion relies on a fluid-filled membrane disposed on the probe tip. This fluid-filled membrane also provides an ideal acoustic window for propagation of the Doppler signal through the latex membrane. Neither aspect interferes with the other and can be packaged within the 7 mm space inside the probe tubing.

A prototype of the probe was assembled and tested to establish that both the shape reconstruction and Doppler blood vessel detection sensors were working as predicted. Although a computer would normally be connected directly to the endoscopic video system, for testing purposes a VHS recording was made of the image obtained from the endoscope. This recording was then played through a VCR plugged directly into an Epix video capture board on a dual-pentium 200 computer. In this way, the shape reconstruction software could access the video images in real time (even though the images were actually recorded earlier, they were still played back in real time) in order to process the images and reconstruct the shape of the membrane.

In these experiments, it was necessary to calibrate the reconstruction software with the correct camera parameters, undeformed dot positions, and threshold values for determining which pixels were black dots and which were white latex. The shape reconstruction software used a 9-by-9 mesh of undeformed points even though there was actually a 3-by-3 mesh of dots drawn on the membrane. The additional dots were obtained by cubic interpolation in 3-space using Matlab finctions. In addition, modifications were made to the shape reconstruction software to change the pixel values of the image outside of a certain field of view to 255 (white) in order to eliminate noise that this unused part of the image was causing. The software was run while the video played at normal speed and the shape of the membrane was correctly reconstructed at approximately 7 Hz. Several sets of data points were taken from the reconstruction and plotted in Matlab to check that the reconstruction that looked correct on the computer screen was in fact reasonable. Examples of undeformed and deformed mesh plot is shown in FIGS. 4a and 4b.

The Doppler aspect of the invention was tested in several ways to ensure that it was working properly. First, the probe was tapped and rubbed with a finger to determine if the transducers were actively sensing movements and hence shifts in the reflected acoustical wave. Thereafter, the probe was dipped into a glass of water and it was able to pick up movements of particles suspended in the water. The amplified speaker produced loud rushing sounds even as the water was disturbed by gently blowing on its surface.

Finally, the probe was tested to evaluate its ability to detect blood flow in pulsing blood vessels. This testing was conducted by simply applying the probe to the radial artery at the wrist and the brachial artery at the crease of the elbow. Because the skin on the outside of the body is not slick with water-based bodily fluids as surfaces found inside the body are during minimally invasive surgery, an aqueous gel was applied to the skin to prevent any air gaps between the tip of the probe and the skin. The result of this testing was a very strong and prominent pulsing sound reproduced by the amplified speaker 52 of the Doppler system. The pulse of the blood vessels was clearly detectable when the probe was placed over the vessels and it stopped as soon as the probe was moved a few millimeters away from the vessels. These tests were conducted with the latex membrane 26 filled with distilled water rather than a preferred gel.

The materials used in construction of the prototype probe were relatively expensive because they were of high quality and because some components such as the special "doughnut" cut transducers had to be specially ordered. Nonetheless, the total material cost for one probe was approximately $250, and construction time was approximately 6 hours. In production, the probe of the invention would be a small fraction of the cost of the endoscope which provides the visual images.

Modifications and variations of the invention will be apparent to those skilled in the art and all such modifications and variations are included within the scope of the appended claims.

What is claimed is:

1. Surgical probe comprising:
    an elongate tube having a tip portion;
    an elastic membrane forming an enclosure on the tip portion and containing a fluid therein, an inside surface of the membrane including a plurality of visible markings;
    apparatus within the tube for illuminating the markings on the inside surface of the membrane;
    means for forming a two-dimensional image of the markings;
    a first ultrasound transducer within the tube for propagating ultrasound energy through the fluid-filled membrane for interaction with and reflection from an object outside the enclosure;
    a second ultrasound transducer within the casing for receiving ultrasound energy reflected from the object;
    a visual display for displaying the markings or a representation derived from the markings to indicate surface topography of a structure in contact with an outside surface of the membrane; and
    a speaker for generating sound related to a frequency shift of the ultrasound energy reflected from the object to indicate motion of the object with respect to the probe.

2. The probe of claim 1 further including computing apparatus for receiving the image from the camera to generate a wire-frame representation of the surface topography.

3. The probe of claim 1 or claim 2 wherein the markings are dots.

4. The probe of claim 3 wherein the dots are arranged in a regular array.

5. The probe of claim 1 wherein the means for forming the image is a camera within the tube.

6. The probe of claim 1 wherein the means for forming the image is a fiber optic bundle delivering light to a camera outside the tube.

7. The probe of claim 5 wherein the camera is charge coupled device.

8. The probe of claim 1 wherein the ultrasound energy is continuous wave ultrasound.

9. The probe of claim 8 wherein the ultrasound energy is centered at approximately 5 MHz.

10. The probe of claim 1 wherein the first and second ultrasound transducers are made of PZt material.

11. The probe of claim 1 wherein the tube is stainless steel.

12. Surgical probe comprising:
    an elongate tube having a tip portion;
    a latex membrane forming an enclosure on the tip portion and containing a gel therein, an inside surface of the membrane including a plurality of visible dots;
    fiber optic apparatus within the tube for illuminating the dots on the inside surface of the membrane;
    a CCD camera within the tube for forming a two-dimensional image of the dots;
    a first ultrasound transducer crystal within the tube for propagating ultrasound energy at approximately 5 MHz through the gel-filled membrane for interaction with and reflection from an object outside the enclosure;
    a second ultrasound transducer crystal within the tube for receiving ultrasound energy reflected from the object;
    a video monitor for displaying the dots or a representation derived from the dots to indicate surface topography of a structure in contact with an outside surface of the membrane; and
    a speaker for generating sound related to a frequency shift of the ultrasound energy reflected from the object to indicate motion of the object with respect to probe.

* * * * *